(12) United States Patent
Reed et al.

(10) Patent No.: US 6,197,013 B1
(45) Date of Patent: Mar. 6, 2001

(54) METHOD AND APPARATUS FOR DRUG AND GENE DELIVERY

(75) Inventors: Michael L. Reed; Lee E. Weiss; Clarence C. Wu; Marc D. Feldman, all of Pittsburgh, PA (US)

(73) Assignee: Setagon, Inc., Charlottesville, VA (US)

( * ) Notice: Subject to any disclaimer, the term of this patent is extended or adjusted under 35 U.S.C. 154(b) by 0 days.

(21) Appl. No.: 08/743,902

(22) Filed: Nov. 6, 1996

(51) Int. Cl.$^7$ .................................................. A61M 31/00
(52) U.S. Cl. ...................... 604/509; 604/103.02
(58) Field of Search ............................. 604/49, 508, 509, 604/103.01, 103.02, 183, 191; 623/1; 606/108, 198

(56) References Cited

U.S. PATENT DOCUMENTS 5,078,736 * 1/1992 Behl .......................................... 623/1
5,569,272   10/1996 Reed et al. .

\* cited by examiner

*Primary Examiner*—A. T. Nguyen
(74) *Attorney, Agent, or Firm*—Ansel M. Schwartz

(57) ABSTRACT

An apparatus for treating a patient. The apparatus includes a deployment mechanism having a surface. The apparatus also includes at least one probe disposed on the deployment mechanism surface. The probe extends between 25 microns and 1000 microns from the surface of the deployment mechanism. The apparatus also includes material coated on the probe. A method for treating a patient. The method includes the steps of placing a material with a probe which extends less than 1000 microns from a surface of a deployment mechanism. Next, there is the step of inserting the probe into preferably a blood vessel of a patient. Then, there is the step of penetrating the interior wall of the vessel from the interior of the vessel with the probe by activating the deployment mechanism so the material can contact the vessel.

9 Claims, 8 Drawing Sheets

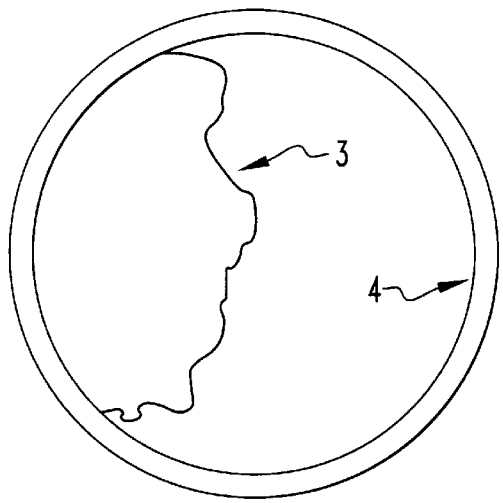
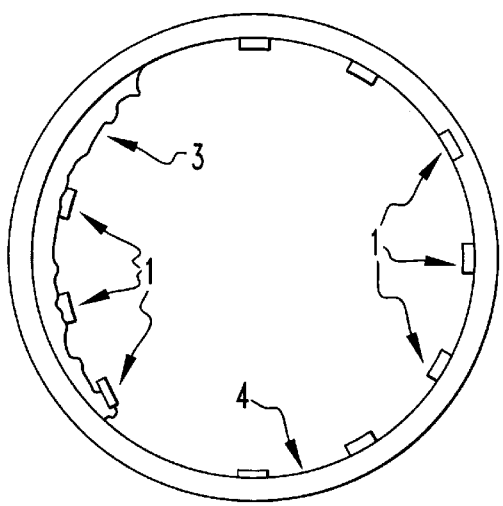
FIG.3a        FIG.3b
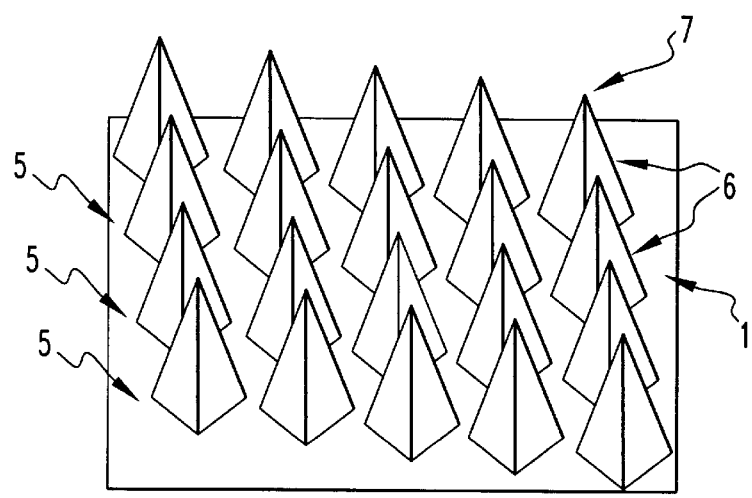
FIG.4

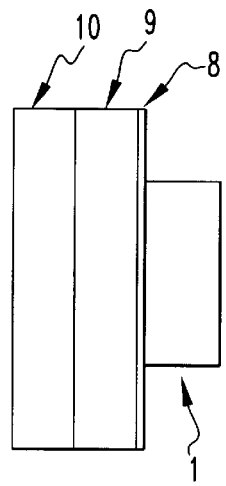
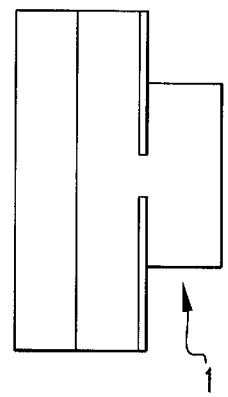
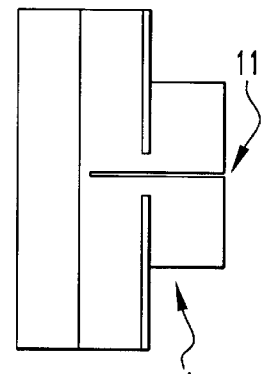
FIG.5a     FIG.5b     FIG.5c
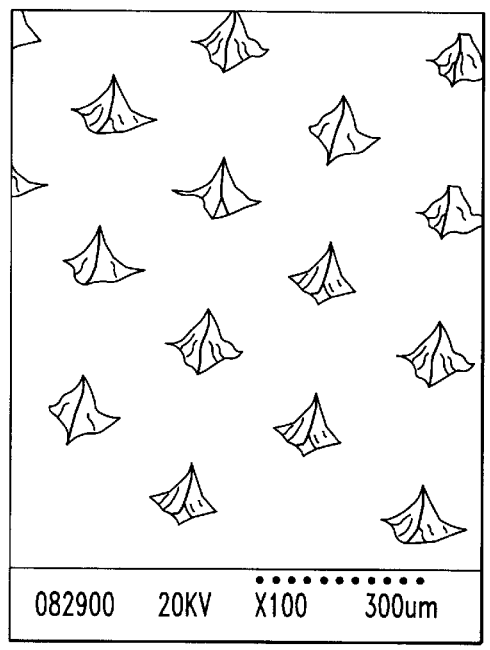
FIG.6

METHOD AND APPARATUS FOR DRUG AND GENE DELIVERY

FIELD OF THE INVENTION

The present invention is related to the treatment of patients with therapeutic agents inside arteries. More specifically, the present invention is related to therapeutic agents that are delivered to arteries through probes that pierce the inside of the arteries.

BACKGROUND OF THE INVENTION

Heart disease continues to be the leading cause of death in the United States. The mechanism of this disease is progressive narrowing of coronary arteries by atherosclerotic plaque which can lead to acute myocardial infarction and disabling angina. One commonly used technique to change the natural history of coronary atherosclerosis is transcatheter therapy, which includes percutaneous transluminal coronary angioplasty, (or PTCA, commonly referred to as balloon angioplasty), atherectomy, and coronary stenting. During these procedures, an expandable balloon, cutting device, or metal cage mounted on a balloon, respectively, is threaded over a pre-placed wire to the site of coronary blockage. In balloon angioplasty, the balloon is inflated, compressing the atherosclerotic plaque; in atherectomy, the plaque is cut away; and in stenting, the device is expanded and deployed against the plaque. In each case, compression of the plaque and expansion of the coronary artery, or removal of the atherosclerotic plaque, restores lumen patency.

Despite the overall initial success of these procedures, approximately 20% to 50% of all patients undergoing these therapeutic procedures to clear blocked coronary arteries will suffer restenosis (re-blockage) within six months of the initial procedure. One widely accepted paradigm is that restenosis is a manifestation of the general wound healing response. The injury induced by coronary intervention causes platelet aggregation, inflammatory cell infiltration and release of growth factors, followed by smooth muscle cell proliferation and matrix formation. In this paradigm, intimal hyperplasia secondary to vascular injury is believed to be the etiology of restenosis. Numerous pharmacological agents and genes have been shown to inhibit restenosis in animal models; however, all have failed in human trials. One explanation for their failure is that suboptimal doses of agents were used in order to prevent side effects which will occur from systemic administration of the higher doses required as shown by animal studies.

The concept of localized intravascular delivery of therapeutics has become an attractive solution to overcome this limitation. Intravascular local delivery devices were recently reviewed by Höfling and Huehns [B. Höfling, T. Y. Huehns, "Intravascular Local Drug Delivery after Angioplasty," European Heart Journal 16, 437–440, 1995]. An illustration of these devices is shown in FIG. 1. The basic principles behind these delivery devices are: diffusion of drugs or genes through close contact; assisted diffusion of drugs or genes driven transmurally by pressure; and transport assisted by physical means. With these devices, successful delivery of pharmacological agents as well as genetic materials have been demonstrated in normal arteries. On the other hand, the atherosclerotic plaque remains a major barrier for this strategy of localized delivery. Delivery of a reporter gene to an atherosclerotic artery was attempted by Feldman et. al. [L. J. Feldman, P G. Steg, L. P. Zheng, "Low-Efficiency of Percutaneous Adenovirus-Mediated Arterial Gene Transfer in the Atherosclerotic Rabbit," Journal of Clinical Investigation 95, 2662–2671, 1995] Compared to normal vessels, the atherosclerotic plaque of the diseased artery behaved as a barrier and resulted in a 10 fold-reduction in transfer efficiency (0.20% vs. 2.0%, p=0.0001).

The only current method which does not rely on passive diffusion is the needle catheter shown in the right lower corner of FIG. 1. It consists of 6 needles which cut through the full thickness of the blood vessel, and deposit a gene or drug in the adventitia (outer layer) of the vessel wall. The adventitia contains the source of the blood supply to the vessel wall, which becomes the means of drug or gene delivery. However, as this catheter transects the vessel wall in an unpredictable fashion, there are serious safety concerns. In addition, since the atherosclerotic plaque will disrupt the blood supply of the coronary artery, predictable, symmetrical delivery of a drug or gene is not certain. In contrast, the present invention allows predictably diffuse delivery of a drug or gene without transection of the coronary artery. The present invention accomplishes this by using a probe of a pre-limited length, as opposed to a standard "long" needle in the needle catheter.

The present invention uses arrays of micromechanical probes which penetrate the plaque and allow for efficient transport of therapeutic agents into the artery media. The probes can be part of a coronary stent which remains in the artery, or can be part of the angioplasty balloon, which is removed after the interventional procedure. Probe height can be varied from less than 25 $\mu$m to over 1000 $\mu$m as required by the thickness of the compressed plaque. This invention differs from conventional methods in that a direct physical penetration of vascular plaque is accomplished. Current delivery techniques rely on diffusion of the drug through a thick layer of plaque; this diffusion is extremely slow, making the transfer ineffective for clinical purposes.

Our preferred embodiment of the invention involves a novel stent design. Stents are devices used after angioplasty to prevent elastic recoil of the compressed plaque. One type, the Palmaz-Schatz stent [Balloon-expandable Palmaz-Schatz coronary stents are manufactured by Johnson & Johnson], is shown in FIGS. 2a and 2b. FIGS. 2a and 2b show a Palmaz-Schatz coronary stent before expansion, after deployment, respectively, in a cardiac artery. The stent consists of a metal lattice, 1, with interstices, 2. First, a conventional balloon angioplasty procedure is performed to create a larger lumen in the occluded vessel. Then, using a second balloon, the stent is inflated at the site of the occlusion to a diameter slightly larger than the normal inner diameter of the vessel. The metal members comprising the stent hold the compressed plaque against the vessel wall, as shown in FIGS. 3a and 3b. FIG. 3a shows plaque build-up, 3, inside coronary artery. FIG. 3b shows after balloon angioplasty and stenting. Therapeutic agents coating the stent, 1, can pass into the vessel wall on the right side, where there is little or no plaque, but are unable to penetrate the plaque built up on the left side of the artery. The thickness of residual plaque in patients with coronary artery disease, following placement of Palmaz-Schatz stents, is generally 100 to 200 $\mu$m. In order to prevent restenosis, genes or drugs placed on the surface of a stent need a means to penetrate the maximal 200 $\mu$m thick layer of compressed plaque barrier to gain entry through the internal elastic lamina into the media where the smooth muscle cells reside. Therapeutic agents placed on the outside of a conventional stent can diffuse into the wall of a normal vessel, but cannot penetrate the plaque.

This problem can be overcome by fabricating the stent such that it has preferably sharp protrusions along the outer surface, FIG. 4. FIG. 4 shows probes, 5, covering the surface of the stent, 1. The probes are protrusions consisting of lateral faces, 6, and sharp tips, 7, which can pierce through the plaque. Therapeutic agents coating the probes can then diffuse into the media layer of the vessel to prevent smooth muscle cell growth and subsequent restenosis. These "probes" can pierce through the plaque, allowing therapeutic agents to find their way into the media layer of the vessel where they are needed. FIGS. 5a, b and c show the transfer of therapeutic agents is greatly enhanced by covering the surface of the stent, 1, with probes, 5. In FIG. 5a, a conventional stent compresses the plaque against the vessel wall, consisting of three layers: the intima, 8, the media, 9, and the adventitia, 10. Transfer of genes into the media depends on diffusion through the plaque, a slow and inefficient process. Texturing the surface with probes, FIG. 5b, allows the gene therapy to penetrate the plaque. In FIG. 5c, the probes are fabricated with a lumen 11, which is in communication with a reservoir.

Recently, Hashmi et. al. [S. Hashmi, P. Ling, G. Hashmi, M. L. Reed, R. Gaugler, W. Trimmer, "Genetic Transformation of Nematodes Using Arrays of Micromechanical Piercing Structures," BioTechniques 19(5), 766–770, 1995] reported the injection of DNA into nematode gonads using probes. These probes, as shown in FIG. 6, were fabricated by anisotropic wet etching of silicon in heights ranging from 10 to over 100 µm. When the nematodes crawled across these probes, they created a path for therapeutics to enter their cells. Successful expression of b-galactosidase, a reporter gene that expresses a blue-green color, was seen in the progeny of the nematodes.

Similar probes have been shown to be able to penetrate both plant cells [W. Trimmer, P. Ling, C.-K. Chin, P. Orton, R. Gaugler, S. Hashmi, G. Hashmi, B. Brunett, M. L Reed, "Injection of DNA Into Plant and Animal Tissues With Micromechanical Piercing Structures," Proceedings of the Eighth International Workshop on Micro Electro Mechanical Systems (MEMS-95), Amsterdam, January 1995, pages 111–115] and blood vessel walls [M. L. Reed, H. Han, L. E. Weiss, "Silicon Micro-Velcro," Advanced Materials 4(1), 48–51, 1992][H. Han, L. E. Weiss, M. L. Reed, "Mating and Piercing Micromechanical Structures for Surface Bonding Applications," Proceedings of the Fourth IEEE Workshop on Micro Electro Mechanical Systems (MEMS-91), Nara, Japan, January 1991, pages 253–258] [R. Dizon, H. Han, A. G. Russell, M. L. Reed, "An Ion Milling Pattern Transfer Technique for Fabrication of Three-Dimensional Micromechanical Structures," IEEE Journal of Microelectromechanical Systems 2(4), 151–159, 1993] and can be used for local drug delivery. A coronary stent with a silicon carbide coating deposited using plasma-enhanced chemical vapor deposition, a common technology used to fabricate microelectromechanical systems (MEMS), has also been reported recently [M. Amon, S. Winkler, A. Dekker, A. Bolz, "Introduction of a New Coronary Stent with Enhanced Radioopacity and Hemocompatibility," Proceedings IEEE Engineering in Medicine and Biology 17, 1995].

SUMMARY OF THE INVENTION

The present invention pertains to an apparatus for treating a patient. The apparatus comprises a deployment mechanism having a surface. The apparatus also comprises at least one probe disposed on the deployment mechanism surface. The probe extends between 25 microns and 1000 microns from the surface of the deployment mechanism. The apparatus also comprises material coated on the probe.

The present invention pertains to a method for treating a patient. The method comprises the steps of placing a material with a probe which extends less than 1000 microns from a surface of a deployment mechanism. Next, there is the step of inserting the probe into a vessel which is preferably a blood vessel of a patient. Then, there is the step of penetrating the interior wall of the vessel from the interior of the vessel with the probe by activating the deployment mechanism so the material can contact the vessel.

BRIEF DESCRIPTION OF THE DRAWINGS

In the accompanying drawings, the preferred embodiment of the invention and preferred methods of practicing the invention are illustrated in which:

FIGS. 3a and FIG. 3b show plaque build-up inside a coronary artery, and after balloon angioplasty and stenting, respectively.

FIG. 4 is a schematic representation of probes of the present invention.

FIGS. 5a, 5b and 5c show a conventional stent against the vessel wall, a probe of the present invention providing for gene or drug therapy, and a probe with the lumen in communication with the reservoir, respectively.

FIG. 6 shows probes of the prior art.

DESCRIPTION OF THE PREFERRED EMBODIMENT

Figure 11:
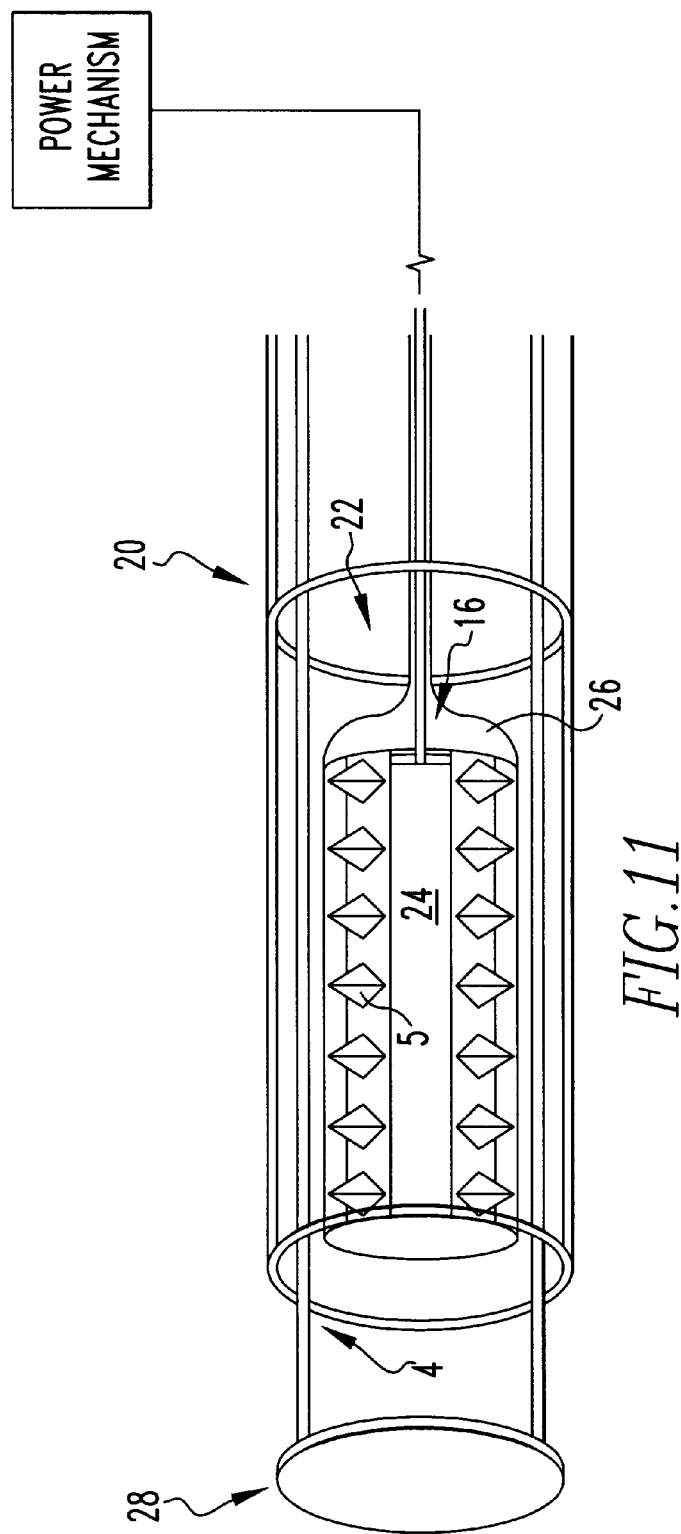
FIG. 11 is a schematic representation of an apparatus of the present invention.

Referring now to the drawings wherein like reference numerals refer to similar or identical parts throughout the several views, and more specifically to FIG. 11 thereof, there is shown an apparatus 20 for treating a patient. The apparatus 20 comprises a deployment mechanism 22 having a surface 24. The apparatus 20 also comprises at least one probe 5 disposed on the deployment mechanism 22 surface 24. The probe 5 extends between 25 microns and 1000 microns from the surface 24 of the deployment mechanism 22. The apparatus 20 also comprises material coated on the probe 5.

Preferably, the apparatus 20 comprises at least a second probe 5 disposed on the surface 24 of the deployment mechanism 22 having material coating on the second probe 5. The spacing between probes can be between 5 and 1000 microns. For spacing where the height of the probe 5 essentially matches the spacing between the probe 5, the fabrication process discussed below can be used. For more dense probe 5 relationships, use of anisotropic dry etching processes accomplishes such increased densities. See H. Jansen, M. de Boer, M. Elwenspoek, "The black silicon method VI: high aspect ratio trench etching for MEMS applications," Proceedings of the Ninth International IEEE Workshop on Micro Electro Mechanical Systems (MEMS-96), San Diego, February 1996, pages 250–257, 1996, incorporated by reference herein.

The deployment mechanism 22 preferably includes a balloon 26 having a surface 24 with the first and second probes disposed on the surface 24 of the balloon 26. Preferably, the deployment mechanism 22 includes a removable housing 28 in which the probes are disposed when the housing is in a closed state, but is separated from the probes when the balloon 26 is in an inflated state.

Preferably, each probe 5 is coated with gold when the material has DNA. Preferably, when the material has DNA, the material is a gene encoding for nitric oxide synthase or vascular endothelial growth factor. Nitric oxide synthase inhibits smooth muscle cells from growing, and inhibits platelet and white blood cell adherence to denuded surfaces following coronary intervention. Vascular endothelial growth factor stimulates reendotheliazation of an injured vessel.

Alternatively, instead of the material having DNA, the material can have a drug, and the material is coated with a biocompatible material which provides a protective coating to prevent the drug or gene from being washed away, and allows for the release of the drug or gene over a period of time. Such coatings include biodegradable materials, hydrogels, and porous ceramics. Such materials as hydrogels can be used with drugs having DNA or not having DNA. The drugs with DNA or without DNA can also be used without such materials or hydrogels. When the material is a drug which does not have the DNA, the material is preferably prednisone or low molecular weight heparin or hirudin. Prednisone inhibits inflammation. Low molecular weight heparin inhibits muscle cell proliferation. Hirudin is an anti-thrombin and thus inhibits the growth of smooth muscle cells or their activation and migration which causes restenosis.

Preferably, each probe 5 has a pointed tip 7. Preferably, each probe 5 is cone shaped. Each probe 5 preferably extends radially from the surface 24 of the balloon 26.

The present invention pertains to a method for treating a patient. The method comprises the steps of placing a material with a probe 5 which extends less than 1000 microns from a surface 24 of a deployment mechanism 22. Next there is the step of inserting the probe 5 into preferably a blood vessel of a patient, although in most places like vessels such as the digestive tract or organs where a catheter can reach, the apparatus 20 can be used. Then there is the step of penetrating the interior wall of the vessel from the interior of the vessel with the probe 5 by activating the deployment mechanism 22 so the material can contact the vessel.

Preferably, the penetrating step includes the step of expanding a balloon 26 of the deployment mechanism 22 on which the probe 5 is disposed until the probe 5 pierces the interior of the vessel wall.

After the insertion step, there is preferably the step of opening a housing 28 in which the probe 5 is disposed. Preferably, the inside of the housing has a hard surface, which the probes 5 do not abrade or stick in. The housing protects the probe 5 and material from body fluid in the patient. Additionally, after the penetrating step, there can be the step of removing the probe 5 from the vessel if it is not necessary or not desired for the probe 5 to remain in place permanently in the vessel wall.

Preferably, in one embodiment, the placing step includes the step of coating the material on the surface of the probe 5. Preferably, the coating step includes the step of putting DNA on the surface of the probe 5, where the surface is made of gold or a material which is both conductive and to which DNA adheres. For instance, after the probe 5 with the DNA pierces the interior of the vessel wall, the probe 5 can be removed from the vessel.

Alternatively, the coating step includes the step of coating the material with hydrogel. Alternatively, the placing step can include the step of filling a lumen 11 on the inside of the probe 5 with the material.

In the operation of the preferred embodiment, micromechanical structures are used to deliver drugs, genes, and other therapeutic agents into blood vessels. The structures are preferably pointed probes which can be integrated with a vascular stent, an angioplasty balloon, or an electrophoretic device. The probes pierce vascular plaque and deliver agents into the vessel wall. A primary application is the delivery of therapies which will prevent restenosis following revascularization procedures such as balloon angioplasty or stent delivery, but other applications are possible (i.e., to deliver secretory agents into the vessel wall, such as therapies to increase the growth of collateral circulation).

Figure 7:
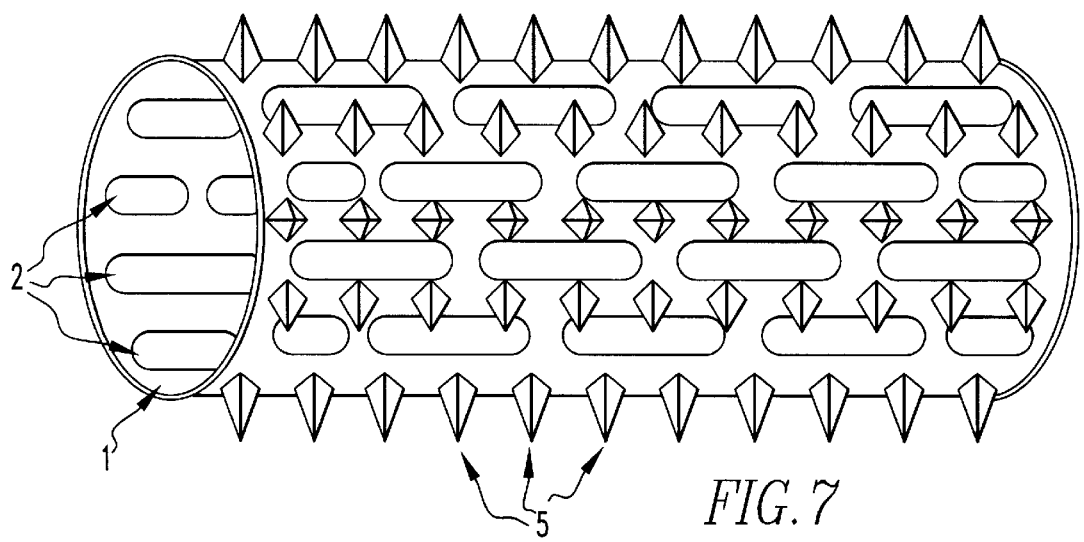
FIG. 7 is a schematic representation of a balloon-expandable probe stent.

The following are several types of embodiments that are part of the apparatus 20:

1) One embodiment is to stud a stent such as a balloon-expandable stent with probes. FIG. 7 shows a balloon-expandable probe stent, 1, which can be expanded due to the presence of interstices, 2. The stent is fabricated with integral micromechanical piercing structures, 5. Coating the stent with the desired drug or gene will inject the drug into the vessel during stent deployment. This embodiment is referred to as a probe stent.

Figure 8:
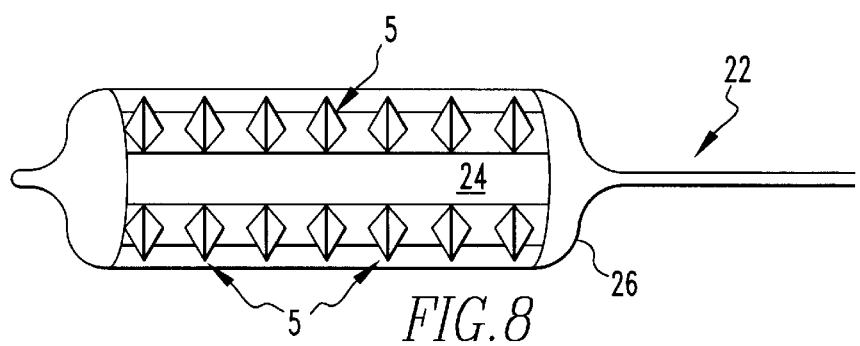
FIG. 8 is a schematic representation of a piercing balloon for drugs or gene therapy.

2) Instead of a stent, a balloon is used to expand an apparatus which injects the drug or gene, but does not remain in the vessel like a stent. For example, longitudinal strips of probes on a flexible backing attached to a balloon. FIG. 8 shows a piercing balloon for intravascular delivery of drug or gene therapy. Strips of material (metal, polyimide, or other materials) with probes are fastened longitudinally along a balloon. When inflated, the balloon forces the probes through the plaque and into the arterial wall, transferring drugs or DNA into the artery media. When deflated, the probes retract and are removed along with the balloon. This arrangement is called a piercing balloon.

Figure 1:
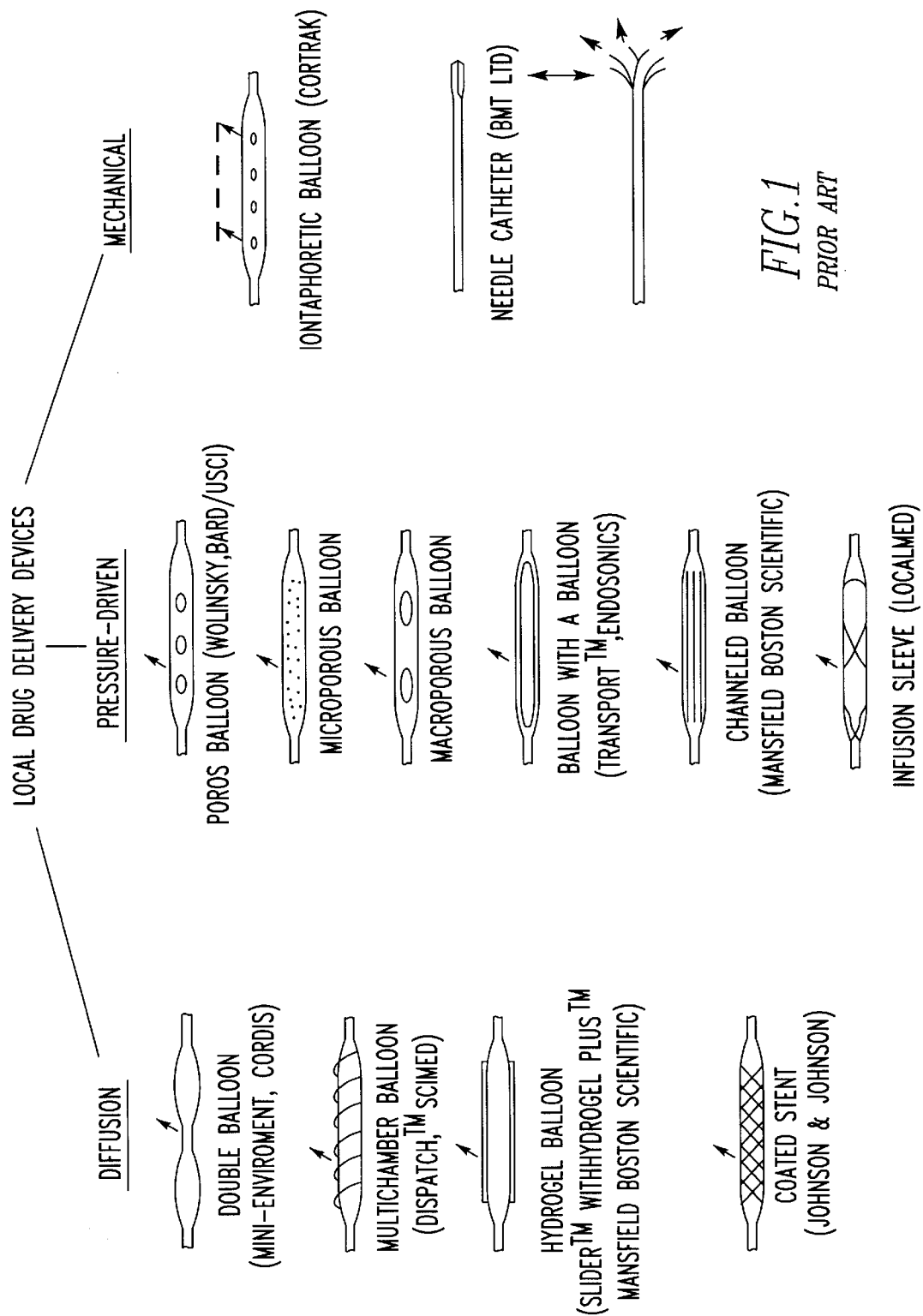
FIG. 1 shows various prior art methods of delivering therapeutic agents to inside coronary arteries.

3) The probes themselves can have lumens, which will allow drugs or genes to be injected from a reservoir. This is an improvement on the class of pressure-driven apparatuses shown in the center column of FIG. 1, where the reservoir is the inflation balloon.

4) The probes can be constructed from a porous material which will create many microminiature reservoirs, which will hold increased amounts of the drug by surface tension. Porous surfaces can be created by anodization of the metal probes, a process which produces a metal oxide with well-ordered arrays of small holes.

5) Another embodiment uses an electric potential to drive the drug from a reservoir into the vessel wall. This iontophoretic technique would especially benefit from the sharp probe tips since electric field is enhanced near an asperity.

6) The apparatuses can be made of metal, or other materials. For example, polymer compounds which dissolve in the body, similar to dissolving sutures commonly used in surgery.

The fabrication techniques for the various embodiments are now described. These methods have in common the fabrication of a template from a crystalline silicon substrate. First, the fabrication of this template wafer is described. Then, it is shown how this wafer is used to build the various types of intravascular delivery apparatuses: a stent covered with probes and the piercing balloon embodiment where the probes are removed after use. In both of these embodiments, the probes can have lumens, and have porous surfaces; methods for creating each of these are described.

Conventional stents are manufactured using electric discharge machining (EDM) of a metal tube. This method is ill-suited to the mass fabrication of probes. A better method is to use silicon micromachining techniques to produce a template from which metal apparatuses with integrated probes are constructed. Such methods are familiar to technologists in the area of microelectromechanical systems and are common for building apparatuses such as pressure sensors and accelerometers. They are detailed in many widely available textbooks, such as "VLSI Fabrication Principles" [S. K. Ghandhi, "VLSI Fabrication Principles," John Wiley and Sons, 1981] and "Semiconductor Sensors" [S. M. Sze "Semiconductor Sensors," John Wiley and Sons, 1994], both of which are incorporated by reference herein. However, because these techniques are not commonly employed in the application described here, a complete description of the process used is given to create the apparatuses for intravascular drug and gene delivery.

The starting material is a crystalline silicon wafer cut from a boule such that the surfaces are (100) oriented planes. This is the standard crystal orientation used for building integrated circuits and as such is widely available. The wafer thickness depends on the height desired for the probes, and should be at least 200 $\mu$m thicker than the probe height. For example, if 200 $\mu$m high probes are desired, the starting wafer should be at least 400 $\mu$m thick. The reason for this is that the final silicon structure must be rigid enough to withstand handling.

The wafer is oxidized in a thermal oxidation furnace (approximately 1000° C.), using a mixture of oxygen and water vapor, so that a film of thermal silicon dioxide ($SiO_2$) is grown on the surface. [S. K. Ghandhi, "VLSI Fabrication Principles," John Wiley and Sons, 1981], incorporated by reference herein. The film must be thick enough to withstand the etching action of a step performed later in potassium hydroxide; a thickness of 1 $\mu$m to 2 $\mu$m is generally sufficient.

The next set of steps are designed to transfer a pattern into the $SiO_2$ layer. A standard photolithographic patterning process is used, which begins with a singe step. The wafer is heated, in air, to a temperature of at least 200° C., in order to drive off loosely bonded water on the $SiO_2$ surface which would otherwise prevent good adhesion of photoresist. Next, the wafer is treated with an adhesion promoter, such as hexamethyldisilizane (HMDS), to help the photoresist layer adhere to the wafer. The adhesion promoter is applied with a spin technique (described below).

Photoresist is applied to the wafer surface by spin coating, or spinning. In this operation, the substrate is placed on a vacuum chuck which holds the wafer in place. Next, a quantity of resist is dispensed from a nozzle while the chuck is rotated at a slow speed. Finally, the speed is ramped up to several thousand rpm which causes all but a thin layer of resist (about 1 to 2 $\mu$m thick) to be thrown off. After a uniform layer of photoresist is deposited, most of the solvents in the photoresist are driven out in the softbake step. This can done either in a convection oven (typically 90° C. for 30 minutes), in an infrared oven ([18]3–4 minutes), on a hotplate (~1 minute), or with a microwave source, which takes only a few seconds. The softbake also improves the adhesion of the photoresist to the substrate.

Figure 9:
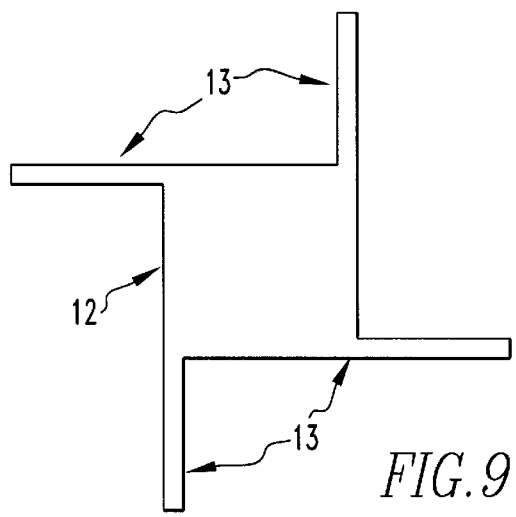
FIG. 9 is a schematic representation of a mask pattern for producing probes.

At this point the wafers are exposed using a mask and exposure tool. The mask consists of a transparent glass plate covered with a regular array of the dark shapes shown in FIG. 9. FIG. 9 shows a mask pattern for producing silicon probes. The silicon under the main square area, 12, is protected from the etchant until convex corner undercutting produces an apex. The corner compensation structures, 13, increase the vertical height achievable with the anisotropic etching process. The shapes consist of a square area, 12, and four rectangular corner compensation structures, 13. The corner compensation structures delay the undercutting of the main square area which occurs during the anisotropic etching process. Inclusion of these structures increases the height of probes attainable using this process. The dimensions of the pattern will vary depending on the desired height of the probes, but are typically 200 $\mu$m across. The wafers are then placed in the exposure tool and aligned so that one long edge of the patterns is parallel to the wafer flat, which in commercially available wafers is always perpendicular to a (011) plane. The photoresist is exposed and developed using standard procedures [S. K. Ghandhi, "VLSI Fabrication Principles," John Wiley and Sons, 1981] [S. M. Sze "Semiconductor Sensors," John Wiley and Sons, 1994], both of which are incorporated by reference herein. The exposure process increases the solubility of the resist in the developer by a large factor, compared to the unexposed areas. Therefore, when the resist is developed, unexposed areas are largely untouched while the exposed portions are quickly washed away. Because the solubility of unexposed resist is finite, careful control of the development process (i.e., developer concentration; development temperature and time) is essential in controlling the pattern dimensions.

After development, the wafer is rinsed, dried, and inspected under a microscope. (Up to this point, the lithographic steps must be performed in a "yellow room" with special illumination to prevent undesired resist exposure. Once the resist is developed, there is no problem with direct white light illumination such as that found in a microscope.) The purpose of this "develop inspect" step is to check for lithography defects such as incomplete development, resist lifting, underexposure or overexposure, and the like. If all is well at this point, then processing proceeds to the next step. If, however, there are problems such as incorrect exposure or development, resist scumming, lifting, or particles, then the resist is reworked. This is accomplished by stripping the resist and returning to the first step. Because the photolithographic processes (up to the etch step) are all low temperature and do not affect the underlying layers, multiple reworks are possible without harm. Photolithography is very sensitive to environmental conditions such as relative humidity, and can even be affected by the level of air pollution. Thus day-to-day variations in exposure and development time, along with a certain percentage of rework, are a normal, expected part of the lithography process.

The wafer now undergoes a hardbake; typical conditions are 150 to 180° C. for 1 hour in a convection oven. The purpose of the hardbake is to remove any remaining solvents and rinse water from the photoresist, and to provide even more adhesion of the photoresist patterns to the substrate.

The back surface of the wafer must be protected with a layer of photoresist or other material during this step to prevent the backside oxide from being stripped during the etching process to be performed next. This is accomplished by spinning a layer of photoresist on the back surface and hardbaking.

The pattern, which has now been transferred from the mask to the photoresist, is now transferred to the $SiO_2$ film. The wafer is immersed in a solution of HF and water, hydrofluoric acid, which selectively attacks the $SiO_2$ film but does not harm the photoresist pattern or the underlying silicon. This step transfers the patterns of FIG. 9 to the oxide layer. Standard practice is to use commercially available buffered HF solutions at room temperature. The wafer is inspected again under a microscope to gauge whether or not the etch process has progressed enough. If insufficient etching has taken place, the wafers can be returned to the etch bath for further processing. Etching is complete when all $SiO_2$ between the patterns has been removed.

The photoresist layers are removed using a convenient method. Standard methods include ashing in an oxygen plasma, or immersion in hot solvents, (i.e. , a sequence of trichloroethane, acetone, and alcohol), or a 4:1 mixture of sulfuric acid and hydrogen peroxide. The last lithographic step is a final inspection under a microscope to verify that all of the photoresist has been removed.

The silicon probes are formed by etching the patterned wafers in a mixture of potassium hydroxide (KOH) and water at 85° C. A typical etchant concentration is a 1:1 volumetric combination of 49% (by weight) KOH solution (a standard commercially available concentration) and water. The etchant temperature must be carefully maintained, using a circulating bath, to produce consistent results. Etching continues until the mask patterns lift off, resulting in a silicon surface studded with an array of pyramidal structures. The time required for etching depends on the probe height, but will be on the order of one hour for 100 μm high probes using the etch conditions outlined here.

The silicon wafer thus processed forms a template for building various embodiments of the intravascular delivery apparatus.

To build a stent with probes, the silicon surface is then coated (on the side with the probes) with a sacrificial layer such as $SiO_2$. This layer can be deposited using RF-magnetron sputtering or chemical vapor deposition (CVD). Using CVD, wafer is introduced into a furnace at approximately 450° C. and exposed to a low pressure atmosphere of silane and an oxidant, whereupon a layer of $SiO_2$ is deposited. [S. K. Ghandhi, "VLSI Fabrication Principles," John Wiley and Sons, 1981, incorporated by reference herein.] This is followed by a thick layer of metal (approximately 100 μm) which can be deposited using a combination of evaporation, sputtering and electroplating, and electroless deposition methods. [S. K. Ghandhi, "VLSI Fabrication Principles," John Wiley and Sons, 1981, incorporated by reference herein] [S. M. Sze "Semiconductor Sensors," John Wiley and Sons, 1994, incorporated by reference herein.].

Figure 2A:
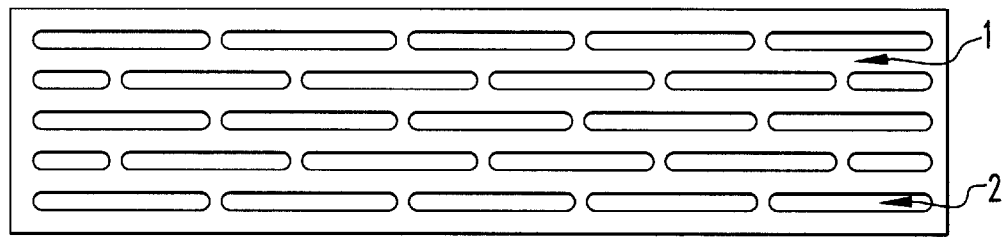
FIGS. 2a and 2b show an ordinary stent before expansion and after deployment, respectively.
Figure 2B:
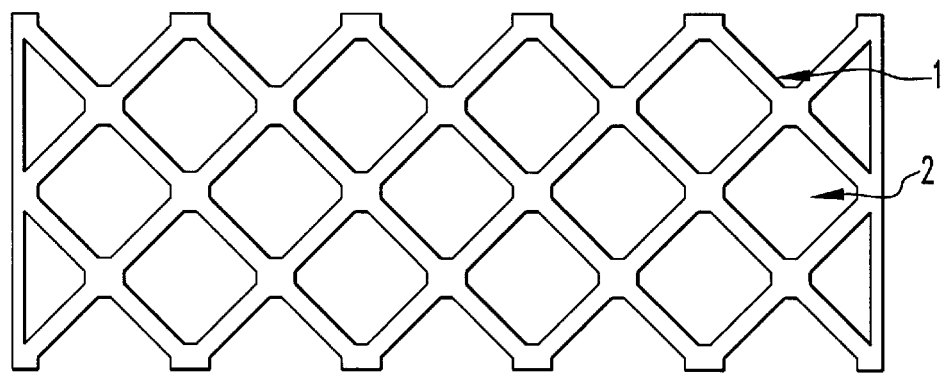

The metal is now patterned using the conventional photolithographic technique described above. The appropriate pattern for a Palmaz-Schatz type stent is a dark-field pattern of long offset rectangles (i.e., the planer version of the cylindrical pattern of FIG. 2). Methods for reproducing a pattern into the metal layer from a lithographic mask are well-known [S. K. Ghandhi, "VLSI Fabrication Principles," John Wiley and Sons, 1981, incorporated by reference herein].

Next, the sandwich of silicon (with probes), sacrificial layer, and patterned metal layer is inserted into an etch bath containing an etchant which will preferentially attack the sacrificial layer. (A sacrificial layer of $SiO_2$ is etched in hydrofluoric acid.) Etching is continued until the patterned metal layer lifts off from the underlying substrate as the sacrificial layer is dissolved. The result is a thin film of metal, with pyramidal protrusions arising from the silicon probes, and long rectangular holes etched during the second lithographic step. The silicon wafer can be recoated with a sacrificial layer and the metal layers and used repeatedly as a template for additional apparatuses.

Finally, the metal lattice is rolled into a cylindrical shape and welded to form the cylindrical stent. One method is to form the lattice around a cylindrical copper mandrel, clamp each end around the mandrel, and use an electron beam welder to join the apparatus along the seam. The metal film can be cut into the appropriate size before rolling, or can be cut after the seam welding process. The process of rolling the metal lattice around the mandrel is essentially that of winding up a roll of metal foil, but for only one turn. Once the film has wrapped around the mandrel, a long blade brought down perpendicular to the mandrel near the point where the two edges meet will provide a guide for the welding process.

Apparatus dimensions depend on the size of the blood vessel where it will be deployed. Typical dimensions are 1–4 cm in length, and 1–6 mm in diameter. The end result is the structure shown in FIG. 7.

Figure 13:
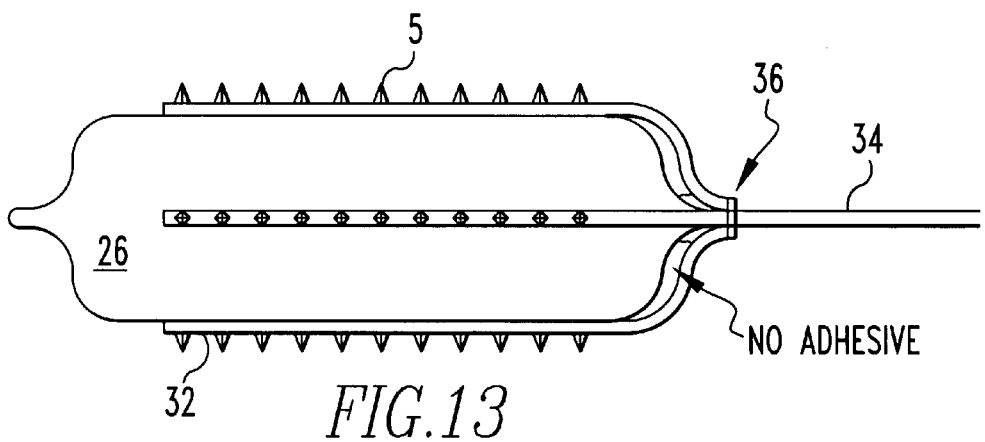
FIG. 13 is a schematic representation of a balloon with strips having a failsafe attachment to a catheter.

To fabricate the piercing balloon embodiment, the silicon template wafer is started with and the procedure is followed for making the probe stent up to the deposition of the thick metal layer. However, the second photolithographic step, which in the case of stents forms a regular array of long holes in the metal, is modified. Instead of making many holes to form a lattice, only a few holes in the metal are produced to allow the etchant to reach the sacrificial layer. The result is a metal film with integral probes (with a few holes). This film is cut into thin strips, approximately 1 cm long and less than approximately 1 mm wide, which are fastened, preferably longitudinally, along a balloon. The strips may be fastened with adhesive along their entire length although no adhesive could be placed on each strip near the distal end so the balloon can more easily expand. See FIG. 8. In the case of adhesive failure, a failsafe attachment can also be made by extending the proximal end of each strip 32 to the distal end of the catheter 34 and attaching the strip to the distal end, as shown in FIG. 13. The distal end can contain a metal band 36 to which the strip is adhered or spot welded. When inflated, the balloon forces the probes through the plaque and into the arterial wall, transferring drugs or DNA into the artery media. When deflated, the probes retract and are removed along with the balloon.

Another method for making this apparatus is to follow the procedure for making the stent, except that the width of the metal struts between the interstices is made smaller. This apparatus is again fastened to the balloon with adhesive. Unlike the stent, which retains its larger diameter when expanded due to plastic deformation of the metal, this apparatus collapses along with the balloon.

Another method to fabricate these apparatuses is to first fabricate a cylindrical mandrel with the probes on the surface. This could be accomplished by employing micro-EDM techniques on a metal tube or rod. The mandrel is then coated (by electroplating, electroless deposition, evaporation, or other techniques) by a conformal layer of metal. Holes for the lattice pattern, 2, can be made with EDM, or a selective deposition technique could be used which results in metal deposition only where it is wanted. After dissolving or otherwise removing the mandrel, the apparatus is released and ready for use.

In both the probe stent and piercing balloon embodiments, it is possible to make the individual probes with lumens. Lumens through the probes provide a channel for drugs, genes, or other therapeutic material to flow from a reservoir such as inside a porous balloon. This increases the amount of material which can be transferred into the blood vessel during a single interventional procedure, compared to simply coating the outside of the probes with the therapy.

To produce probes with lumens, the above procedure is modified. Before patterning the metal layer (i.e., the second lithographic step), the tips of the probes are abraded using a mechanical polishing wheel. This removes the metal at the very tips of the probes, yet leaves a sharp structure capable of penetrating the plaque.

To increase the amount of drugs or genes held by the apparatus, the structural material could be made porous. A straightforward way of accomplishing this goal is to anodize the metal forming the apparatus. Anodization produces a high density of small, vertically oriented pores, of which the size and configuration can be controlled by varying the anodization current, temperature, and solution concentration.

The probes themselves are coated with a thin (<1 $\mu$m) layer of gold which is well known to have desirable properties for attracting and holding DNA. The gold coating can be applied at different stages of manufacture, using various standard processes. For example, the silicon template wafer, after the sacrificial layer is applied, can be coated with gold using a standard evaporation or sputtering process. Subsequent structural layers of metal can then be plated using the gold as a seed layer. Alternatively, the gold can be physically deposited at a later stage, such as after stent formation and welding.

The fabrication processes described here illustrate intravascular delivery apparatuses made from metal. Commercially available stents are made from metals chosen for their mechanical properties and biocompatibility. These same considerations apply to the apparatuses described here. Suitable modifications to the preceding processes can be employed to fabricate apparatuses made from other materials. For example, polyimides are commonly used in MEMS technology and can be easily employed for this application as well. Dissolvable polymers which are used in surgery are another possibility. Biodegradable polymers such as polylactide, polyglycolide, and polyorthoster can be used to carry drugs, thus stents wholly or partially made from these materials will release therapy over an extended period.

An important feature of this invention is the probes which pierce through the atherosclerotic plaque and deliver drug or gene therapy to the artery media. These probes can either be part of a stent, or attached to the balloon. Gene or drug therapy can be applied either to the surface of the probe or delivered through a hollow probe. The drug or gene can either be applied acutely during several minutes of balloon inflation, or left in place permanently by normal deployment of the stent.

After manufacture, the apparatuses are sterilized and stored until ready for use. When needed, the apparatuses would first be coated with the desired drug or gene therapy material. This can be accomplished by dipping, spraying, spinning, or rolling the apparatuses with a liquid or gel containing the therapeutic material. To prevent the therapeutic material from washing off in the bloodstream, one or more means can be employed: (1) a protective sheath, preferably with a hard interior surface, covers the entire apparatus, which is retracted when the apparatus is about to be deployed at the site in the artery; (2) a coating of a biocompatible material which provides a protective coating to prevent the drug or gene from being washed away, and allows for the release of the drug or gene over a period of time, such as hydrogel applied to the probes on top of the therapeutic material to cover and hold the drug or genes in place. The hydrogel will dissolve in the circulatory system over an extended period, slowly allowing the drug or gene to be deployed.

Application of the probe stent will be performed via standard catheterization techniques. These methods are well known to cardiac physicians and are described in detail in many standard references [D. S. Baim, W. Grossman (editors), "Cardiac Catheterization, Angiography and Intervention," 5th edition, William & Wilkins, 1996, incorporated by reference herein] [S. G. Ellis, D. R. Holmes, Jr., "Strategic Approaches in Coronary Intervention," William & Wilkins, 1996, incorporated by reference herein]. In brief, percutaneous access of the femoral or brachial arteries is obtained with standard needles, guide wires, sheaths, and catheters. After engagement of the coronary arteries with a hollow guiding catheter, a wire is passed across the coronary stenosis where the probe stent or piercing balloon is to be deployed. The apparatus is then passed over this wire, using standard coronary interventional techniques, to the site of atherosclerotic coronary plaque where drug or gene therapy is to be delivered.

Figure 12:
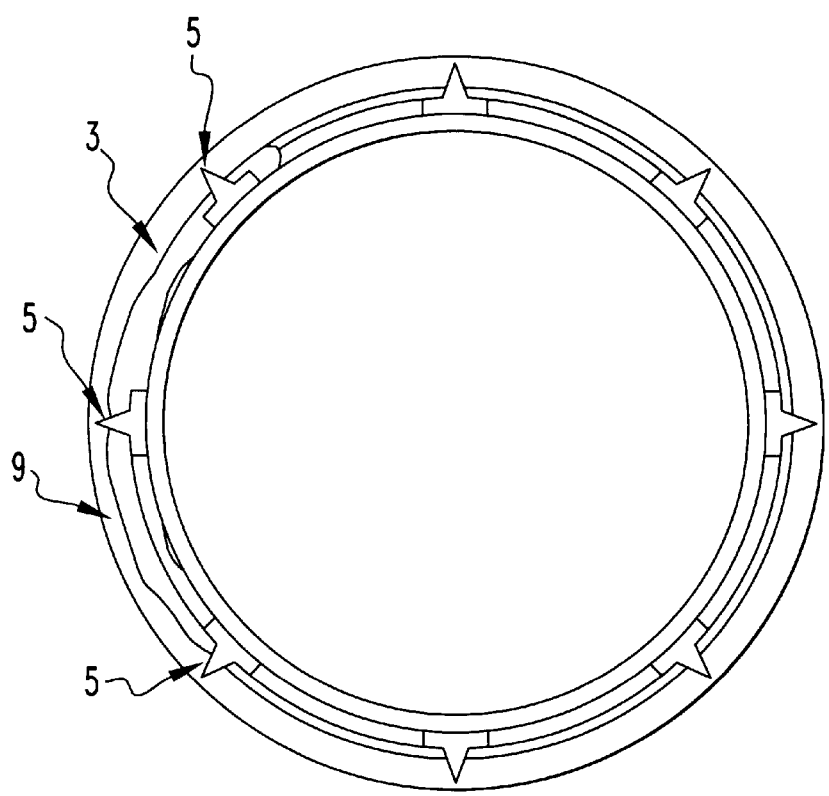
FIG. 12 is a schematic representation of a cross-sectional view of a portion of the apparatus with probes piercing the vessel.

Immediately prior to balloon inflation, a protective sheath is retracted to expose the probes to the diseased vessel wall. (This protective sheath is a standard component of current stents, such as the Palmaz-Schatz stent manufactured by Johnson & Johnson, and recently approved for clinical use by the FDA.) The balloon is then inflated to force the probes through the atherosclerotic plaque, so the probe tips reach the media portion of the vessel wall, as shown in FIG. 12. FIG. 12 shows a cross-sectional view of drug or gene delivery apparatus expanded inside a blood vessel. Probes, 5, pierce through the layer of compressed plaque, 3, and into the vessel media, 9. This allows for efficient transfer of material into the blood vessel. Balloon inflation is performed using standard interventional techniques. The therapeutic material which coats the probe tips now enters the artery media, where it performs its desired biological function.

The apparatus has now performed its task, delivery of drug or gene therapy through atherosclerotic plaque into the vessel wall. In the case of the probe stent, the stent is deployed permanently, and the deploying balloon and wire are removed. Probes mounted directly on a balloon are removed when the balloon is deflated with negative pressure.

Figures 10A, 10B, 10C:
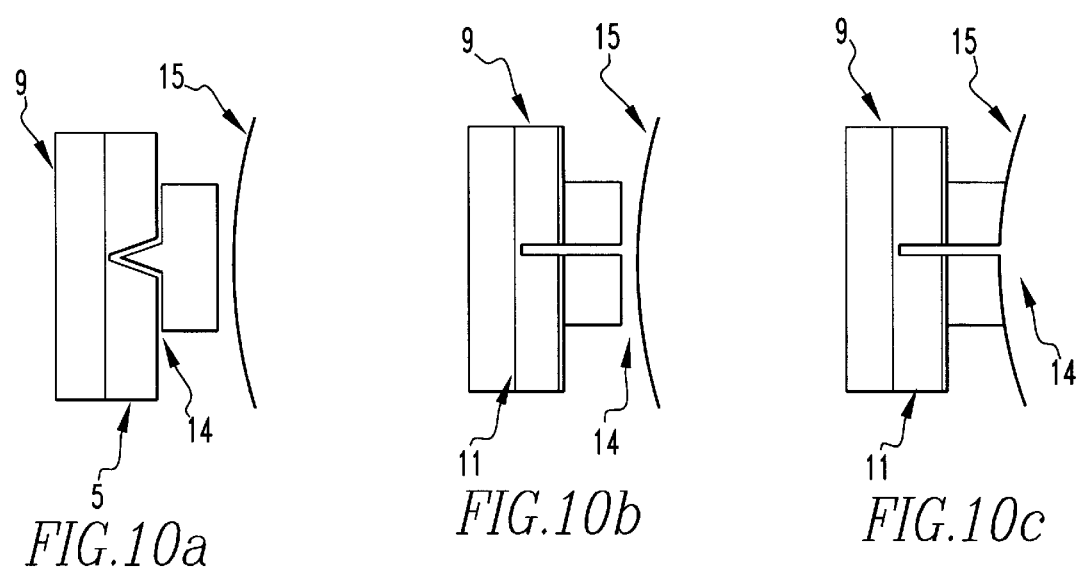
FIGS. 10a, 10b and 10c depict a probe piercing a vessel, a probe which contains a lumen piercing a vessel, and the probe with a lumen where the balloon has expanded so that fluid is forced through the probe, respectively.

Probes with lumens are employed using the same procedure, except that a reservoir of drug or gene therapy is provided so that a larger supply of material can be delivered more acutely to the vessel. Apparatuses with lumens through the probes can use a porous balloon containing the drug or gene therapy which would be pumped through the lumens during the procedure. A reservoir is created by coating the underside of the apparatus (i.e., the side away from the probe tips) with a viscous liquid or gel containing the drug or gene therapy; the lumens through the probes provide a pathway for material from the reservoir into the vessel wall. The various means by which drug or gene therapy is delivered to the vessel, in apparatuses with and without lumens, is illustrated in FIGS. 10a, b and c. FIGS. 10a, b and c show three mechanisms for transferring drug or gene therapy, 14, into the vessel media, 9, using a probe, 5. FIG. 10a shows a probe, 5 (without a lumen) pierces the vessel, when balloon, 15, expands to the left. This provides a pathway for the drug or gene therapy, coating the probe, to enter the vessel. In FIG. 10b, there is shown a probe which contains a lumen 11, which holds the drug or gene therapy 14, by surface tension. The lumen can have a diameter between 5 microns and 100 microns through the probe. Additional therapy is in reserve in a liquid or gel reservoir between the probe and expansion balloon. When the balloon, 15, is expanded, this forces therapy from the reservoir through the lumen. In the embodiment shown in FIG. 10c, the reservoir is inside the expansion balloon, 15. The probe lumen extends through the balloon so that fluid forces used to expand the balloon also force additional therapy through the lumen. In general, the technology existing regarding angioplasty and the sizes typically used of balloons, stents, etc. are applicable to the apparatus here.

A probe carrying apparatus can have an electrical connection with a power mechanism, carried down the guiding catheter, which would place the apparatus at an electrical potential with respect to a counterelectrode placed elsewhere in or on the patient. FIG. 11 shows a cutaway diagram of a delivery apparatus inside a blood vessel, 4. Current supplied through a wire, 16, connected to the conducting drug or gene delivery apparatus causes enhanced iontophoretic transfer of the therapy through the probe points. Note, the wire need not be connected to the probes. If the probes are in place (i.e. the stent) another catheter with an electrode can be inserted which carries the current. A small current through the resulting circuit will drive charged drugs or genes, through iontophoresis, into the vessel wall. Typical current densities for this method are in the range of 2–8 mA/cm$^2$ and would remain on long enough (possibly up to 6 hours) for the drug or genes to effectively transfer from the probe 5 to the vessel. A large increase in drug or gene uptake occurs using this technique since much larger driving forces (i.e., electric fields) are produced near the sharp tips of the probes, compared to a conventional iontophoretic balloon. While the apparatus 20 works without any electrical connection or electrical potential, such electrical means is an additional feature which facilitates greater control over the movement of the drugs, whether the drugs are with or without genes or DNA or RNA or nucleic acid in general.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for treating restenosis in a vessel of a patient comprising the steps of:

placing a material with a probe, said probe extending outwardly from its central axis less than 1000 microns from an outer surface of a deployment mechanism;

inserting the probe into a vessel of patient;

activating the deployment mechanism;

penetrating the interior wall of the vessel from the interior of the vessel with the probe on the outer surface of the deployment mechanism so the material can contact the vessel; and delivering the material to the vessel wall.

2. A method as described in claim 1 wherein the inserting step includes the step of inserting the probe into a blood vessel of a patient.

3. A method as described in claim 2 wherein the penetrating step includes the step of expanding a balloon of the deployment mechanism on which the probe is disposed until the probe pierces the interior of the vessel wall.

4. A method as described in claim 3 wherein the placing step includes the step of coating the material on the surface of the probe.

5. A method as described in claim 4 wherein the coating step includes the step of putting DNA on the surface of the probe, where the surface is made of gold or a material which is both conductive and to which DNA adheres.

6. A method as described in claim 4 including after the penetrating step, there is the step of removing the probe from the vessel.

7. A method as described in claim 4 wherein the coating step includes the step of coating the material with hydrogel or other biocompatible material which provides a protective coating to drugs or DNA.

8. A method as described in claim 3 wherein the placing step includes the step of filling a reservoir on the inside of the probe with the material.

9. A method as described in claim 1 wherein after the inserting step there is the step of opening a housing in which the probe is disposed, said housing protecting the probe and material from body fluid in the patient.

* * * * *